US005624905A

United States Patent [19]
Engvall et al.

[11] Patent Number: 5,624,905
[45] Date of Patent: Apr. 29, 1997

[54] MEROSIN FRAGMENTS AND USES THEREOF

[75] Inventors: Eva Engvall, Rancho Santa Fe, Calif.; Ilmo Leivo, Helsinki, Finland

[73] Assignee: La Jolla Cancer Research Foundation, La Jolla, Calif.

[21] Appl. No.: 393,250

[22] Filed: Feb. 23, 1995

Related U.S. Application Data

[63] Continuation of Ser. No. 103,032, Jul. 8, 1993, abandoned, which is a continuation of Ser. No. 734,201, Jul. 22, 1991, abandoned, which is a division of Ser. No. 472,319, Jan. 30, 1990, abandoned.

[51] Int. Cl.$^6$ .......................... A61K 38/00; A61K 38/39; G01N 33/567; C07K 14/78
[52] U.S. Cl. ................................ 514/21; 514/2; 530/350; 530/389.2; 530/399; 530/839; 436/503
[58] Field of Search .......................... 435/252.3, 172.3, 435/69.1; 530/350, 389.2, 399, 839; 436/547, 63, 64, 503; 514/2, 21

[56] References Cited

PUBLICATIONS

Leivo et al Ontogenesis vol 20, 1989, Translation.

Ehrig et al Annals of the New York Acad of Science vol 580. pp. 276–280, 1989 Presented at the N.Y.A. Science Conf on Collogen 1989.

Leivo et al Lab Investigation 61:426–432 1989.

Manthrope. et al, Monualy the Nervos Syst pp. 322–326 1989.

Ehrig et al, Annals of the New York Aead. of Scie vol 580. pp 276–280, 1989 Presented at the N.Y.A Science Conf on Collogen 1989.

Leivo et al, Lab Invest 61:426–432 1989.

Manthrope et al Manual of the Nervous Syst. pp 32–326 1989.

David Edgar et al., Structural Requirements for the Stimulation of Neurite Outgrowth by Two Variants of Laminin and Their Inhibition by Antibodies, The Journal of Cell Biology 106.1299–1306 (1988).

Ohno, M., et al. "Isolation of Laminin From Human Placental Basement Membranes: Amnion, Chorion, and Chorionic Microvessels", Chemical Abstracts, vol. 98, No. 25, Jun. 20, 1983, p. 365, abstract 213310m.

Engvall, E., et al., "Distribution and Isolation of Four Laminin Variants: Tissues Restricted Distribution of Heterotrimers Assembled From Five Different Subunits", Chemical Abstracts, vol. 114, No. 9, Mar. 4, 1991; p. 461, abstract 79023r.

Deutzmann, R., et al., "Structural Study of Long Arm Fragments of Laminin: Evidence for Repetitive C–terminal Sequences in the A–chain, Not Present in the B–chains", Eur. J. Biochem. 177:35–45 (1988).

Martin, G.R. et al., "Laminin and Other Basement Membrane Components", Ann. Rev. Cell Biol. 3:57–85 (1987).

Leivo, I., et al., "Merosin, A Protein Specific for Basement Membranes of Schwann Cells, Striated Muscle, and Trophoplast, Is Expressed Late in Nerve and Muscle Development", Proc. Natl. Acad. Sci. USA 85:1544–48 (1988).

Lander, A.D., et al., "Laminim is Associated with the 'Neurite Outgrowth–promoting Factors' Found in Conditioned Media", Proc. Natl. Acad. Sci. USA 82:2183–87 (1985).

Davis, G.E., et al., "Isolation and Characterization of Rat Schwannoma Neurite–promoting Factor: Evidence that the Factor Contains Laminin", J. Neurosci. 5:2662–71 (1985).

Steele, J.G., et al., "Neurite–Promoting Activity From Fetal Skeletal Muscle: Partial Purification of a High–Molecular–Weight Form", J. Neurosci. Res. 15:323–39 (1986).

Sandrock, A.W., et al. "Identification of a Peripheral Nerve Neurite Growth–promoting Activity by Development and Use of an *in Vitro* Bioassay", Proc. Natl. Acad. Sci. USA 84:6934–38 (1987).

Edgar, D., at al., "Structural Requirements for the Stimulation of Neurite Outgrowth by Two Variants of Laminin and Their Inhibition by Antibodies", J. Cell Biol. 106:1299–306 (1988).

Hunter, D.D., et al., "A Laminin–like Adhesive Protein Concentrated in the Synaptic Cleft of the Neuromuscular Junction", Nature 338:229–33 (1989).

Cornbrooks, C.J., et al., "*In Vivo and In Vitro* Observations on Laminin Production by Schwann Cells", Proc. Natl. Acad. Sci. USA 80:3850–54 (1983).

Hassell, J.R., et al., "Isolation of Two Forms of Basement Membrane Proteoglycans", J. Biol. Chem. 260:8098–8105 (1984).

Engvall, E., et al., "Merosin is a Tissue–restricted Basement Membrane Component and a Member of a Family of Laminin–like Protein", J. Cell Biol. 109: 4 part 2, (New York), Twenty–Ninth Annual Meeting of the American Society for Cell Biology, Houston, TX, Nov. 5–9, 1989, Minisymposium 1, Abstract 3.

Ehrig, K., et al., "Merosin, A Tissue–Specific Basement Membrane Protein, is a Laminin–like Protein", Proc. Natl. Acad. Sci. USA 87:3264–68 (1990).

Hagg, T., et al. "Merosin is Associated with Neurons of the Adult Mammalian Nervous System", J. Cell Biol. 111: 5 part 2, (New York), Abstract 2227 (1990).

Engvall et al., "Merosin promotes cell attachment and neurite outgrowth and is a component of the neurite–promoting factor of RN22 Schwannoma cells" E. Cell Res. 198:115–123 (1992).

(List continued on next page.)

*Primary Examiner*—Hazel F. Sidberry
*Attorney, Agent, or Firm*—Campbell & Flores LLP

[57] ABSTRACT

This invention provides a purified protein, having an apparent molecular weight of about 800 kDa, designated merosin. Also provided is an isolated nucleic acid sequence which encodes merosin. The invention further provides antibodies, vectors, and the expression of recombinant proteins by use of a host vector system. The invention also provides the use of merosin to promote neurite growth and for certain diagnostic applications.

1 Claim, 7 Drawing Sheets

PUBLICATIONS

PCT/US91/00631 Jan. 30, 1991 PCT Search Report.

George R. Martin and Rupert Timpl, Laminin and Other Basement Membrane Components, Ann. Rev. Cell Biol. 3:57–85 (1987).

Ilmo Leivo and Eva Engvall, Merosin, a protein specific for basement membranes of Schwann cells, striated muscle, and trophoblast, is expressed late in nerve and muscle development, Proc. Natl. Acad. Sci. USA 85:1544–1548 (1988).

Arthur D. Lander et al., Laminin is associated with the "neurite outgrowth–promoting factors"found in conditioned media, Proc. Natl. Acad. Sci. USA 82:2183–2187 (1985).

George E. Davis et al., Isolation and Characterization of Rat Schwannoma Neurite–promoting Factor: Evidence that the Factor Contains Laminin[1], The Journal of Neuroscience 5:2662–2671 (1985).

J.G. Steele and H. Hoffman, Neurite–Promoting Activity From Fetal Skeletal Muscle: Partial Purification of a High–Molecular–Weight Form, Journal of Neuroscience Research 15:323–339 (1986).

Alfred W. Sandrock, Jr., and William D. Matthew, Indentification of a peripheral nerve neurite growth–promoting activity by development and use of an *in vitro* bioassay, Proc. Natl. Acad. Sci. USA 84:6934–6938 (1987).

Paulsson et al., "Structure of Laminin Variants—The 300–kDa chains of murine and bovine heart laminin are related to the human placenta merosin heavy chain and replace the A chain in some laminin variants" *J. Biol. Chem.* 266:17545–17551 (1991).

Wewer et al., "Human Laminin Isolated in an Nearly Intact, Biologically Active Form from Placenta by Limited Proteolysis" *J. Biol. Chem.* 258:12654–12660 (1983).

Hayashi and Miki, "Purification and Characterization of a Neurite Outgrowth Factor from Chicken Gizzard Smooth Muscle" *J. Biol. Chem.* 260:14269–14278 (1985).

Palm and Furcht, "Production of Laminin and Fibronectin by Schwannoma Cells: Cell–Protein Interactions In Vitro and Protein Localization in Peripheral Nerve In Vivo" *J. Cell Biol.* 96:1218–1226 (1983).

Terranova et al., "Laminin promotes rabbit neutrophil motility and attachment," *J. Clin. Invest.* 77:1180–1186 (1986).

Paulsson and Saladin, "Mouse heart laminin," *J. Biol. Chem.* 264:18726–18732 (1989).

Manthorpe et al., "A dissection of tissue culture," *Manual of the Nervous System,* pp 322–326 (1989).

Leivo et al., "Distribution of merosin, a laminin–related, tissue–specific basement membrane protein, in human schwann cell neoplasms," *Laboratory Invest.* 61:426–432 (1989).

Ohno et al., "Laminin M is found in placental basement membranes, but not in basement membranes of neoplastic origin" *Conn. Tissue Res.* 15:199–207 (1986).

FIG. 3a   FIG. 3b   FIG. 3c
 1   2     1   2     lam a-pept      mab      a-lam

FIG. 4C-1 ns/patent text/

MEROSIN FRAGMENTS AND USES THEREOF

The present invention was supported by grants DK 30051, CA 45546, CA 28896 and Cancer Center Support Grant CA30199 from the National Institute of Health. The United States Government may have rights in the invention.

This application is a continuation of application Ser. No. 08/103,032, filed Jul. 8, 1993, now abandoned, which is a continuation of application Ser. No. 07/734,201, filed Jul. 22, 1991, now abandoned, which is a divisional of application Ser. No. 07/472,319, filed Jan. 30, 1990, now abandoned.

BACKGROUND OF THE INVENTION

This invention relates generally to basement membranes and specifically to a novel tissue-specific basement membrane-associated protein.

Basement membranes are thin sheets of extracellular matrix separating epithelial cells from underlying tissue stroma. They compartmentalize epithelial and endothelial organs and maintain tissue structures. In some tissues the basement membrane is a product of the interaction of several cell types; for example, the glomerular basement membrane is made by both epithelial and endothelial cells. In skeletal muscle, fibroblasts from the endomysium contribute type IV collagen to the assembly of the basement membrane. The formation of the neural basal lamina requires the interaction of Schwann cells and neurons. Further, basement membranes function in development and tissue repair by promoting attachment, migration and proliferation of cells and by mediating signals for tissue interactions.

All basement membranes contain laminin, type IV collagen, entactin and heparan sulfate proteoglycan. Laminin is a large glycoprotein composed of three polypeptide chains, a 400 kD A chain and two B chains of about 200 kD. The amino-terminal two thirds of the A chain is homologous to the B1 and B2 chains while the carboxy-terminal third has a distinct structure. Laminin promotes attachment, spreading, motility and growth of a variety of cell types. One of the most striking features of laminin is its capacity to promote outgrowth of neurites from cultured neuronal cells. A major site of cell adhesion and the neurite-promoting activity appear to reside in the globular domain at the end of the long arm of this molecule.

The metastatic propensity of certain tumor cells may also be influenced by laminin. For example, laminin has been shown to mediate the attachment of malignant carcinoma cells to type IV collagen and to increase the metastatic potential of murine melanoma cells. Other basement membrane proteins and their receptors may be involved in the adhesion of metastasizing tumor cells to basement membranes of blood vessels and other epithelial tissues.

The Leivo and Engvall reference, Proc. Natl. Acad. Sci. USA, 85: 1544–1548 (1988), incorporated by reference herein, recently described the isolation of a 65-kDa and an 80-kDa precursor, basement membrane-associated protein which was termed merosin. However, there was no disclosure of the approximately 800 kDa protein described herein. Since this 65-kDa and 80-kDa proteins appear to be subunits of the 800 kDa protein, the term "merosin" has now also been applied to the 800 kDa protein described herein.

Because of the critical role of basement membranes in development, tissue repair, neurite growth and cancer, there exists a need for the identification of new basement membrane components. The present invention satisfies this need.

SUMMARY OF THE INVENTION

This invention provides a purified protein, having an apparent molecular weight of about 800 kDa, designated merosin. Also provided is an isolated nucleic acid sequence which encodes merosin. The invention further provides antibodies, vectors, and the expression of recombinant proteins by use of a host vector system. The invention also provides the use of merosin to promote neurite growth.

DETAILED DESCRIPTION OF THE INVENTION

This invention provides a novel protein, designated merosin, which is structurally related to laminin. The protein has an apparent molecular weight of about 800 kDa and is composed of four polypeptides having apparent molecular weights of 300, 200, 200 and 80 kDa, the 300 kDa polypeptide being joined to the 200 kDa polypeptides by disulfide bonds and the 300 kDa and 80 kDa polypeptides having substantially the amino acid sequence shown in FIG. 1. Merosin is found in placenta, striated muscle, peripheral nerve, trophoblasts and human Schwann cell neoplasms. Merosin is not present in the fetus and only appears in muscle and nerve after birth.

It is understood that limited modifications may be made without destroying the biological function of merosin, and that only a portion of the entire primary structure may be required in order to effect activity. For example, the merosin protein of the invention has an amino acid sequence substantially similar to that shown in FIG. 1, but minor modifications of this sequence which do not destroy its activity also fall within the definition of merosin and within the definition of the protein claimed as such. Moreover, fragments of the sequence of FIG. 1, but not including the previously described 80 kD fragment which retain the function of the entire protein are included within the definition. It is understood that minor modifications of primary amino acid sequence may result in proteins which have substantially equivalent or enhanced function as compared to the sequence set forth in FIG. 1. These modifications may be deliberate, as through site-directed mutagenesis, or may be accidental such as through mutation in hosts which are merosin producers. All of these modifications are included as long as merosin, biological function is retained. Further, various molecules can be attached to merosin, for example, other proteins, carbohydrates, or lipids. Such modifications are included within the definition of merosin.

"Purified", when used to describe the state of merosin, denotes the protein free of a portion of the other proteins and molecules normally associated with or occurring with merosin in its native environment.

"Isolated" when used to describe the state of the nucleic acids encoding merosin, denotes the nucleic acids free of at least a portion of the molecules associated with or occurring with nucleic acids in the native environment.

"Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Host-vector system" refers to cells which have been transfected with vectors constructed using recombinant DNA techniques. The vectors and methods disclosed herein are suitable for use in host cells over a wide range of prokaryotic and eukaryotic organisms.

Reference is made to standard textbooks of molecular biology that contain definitions and methods and means for carrying out basic techniques, encompassed by the present invention. See, for example, Maniatis et al., *Molecular Cloning: A Laboratory Manual*, Cold Spring Harbor Laboratory, N.Y. (1982) and the various references cited therein. This reference and the cited publications are hereby expressly incorporated herein by reference.

In addition, recombinant DNA methods currently used by those skilled in the art include the polymerase chain reaction (PCR) which, combined with the synthesis of oligonucleotides, allows easy reproduction of DNA sequences. A DNA segment of up to approximately 6000 base pairs in length may be amplified exponentially starting from as little as a single gene copy by means of PCR. In this technique a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202 all of which are incorporated by reference herein.

Figure 1B:
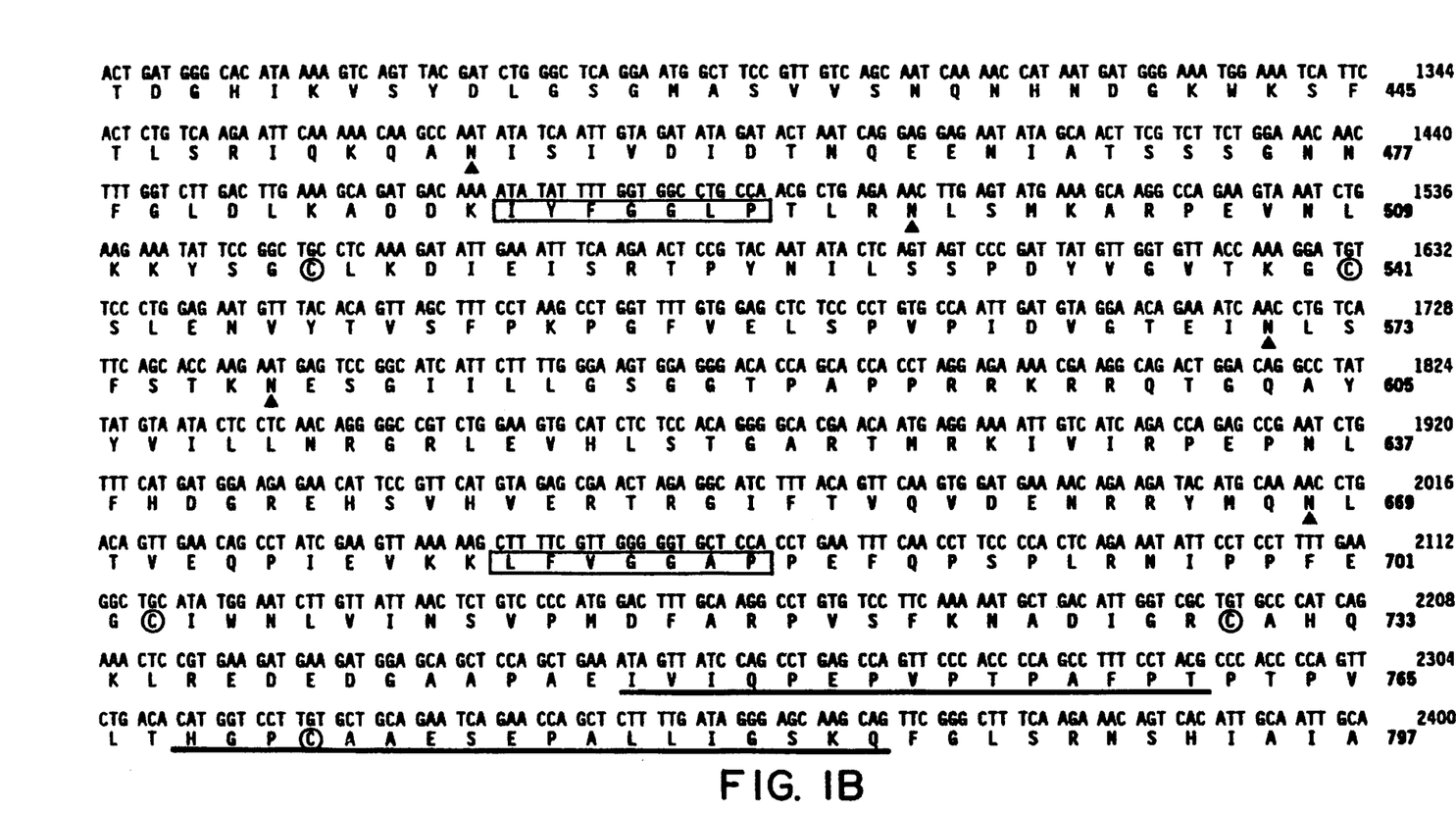
FIG. 1 shows the DNA sequence of merosin cDNA and the deduced amino acid sequence. Potential N-glycosylation sites are indicated by (▲) and cysteines are circled. Sequences obtained by amino acid sequencing are underlined. Conserved motifs of amino acid sequence are boxed.
Figure 2:
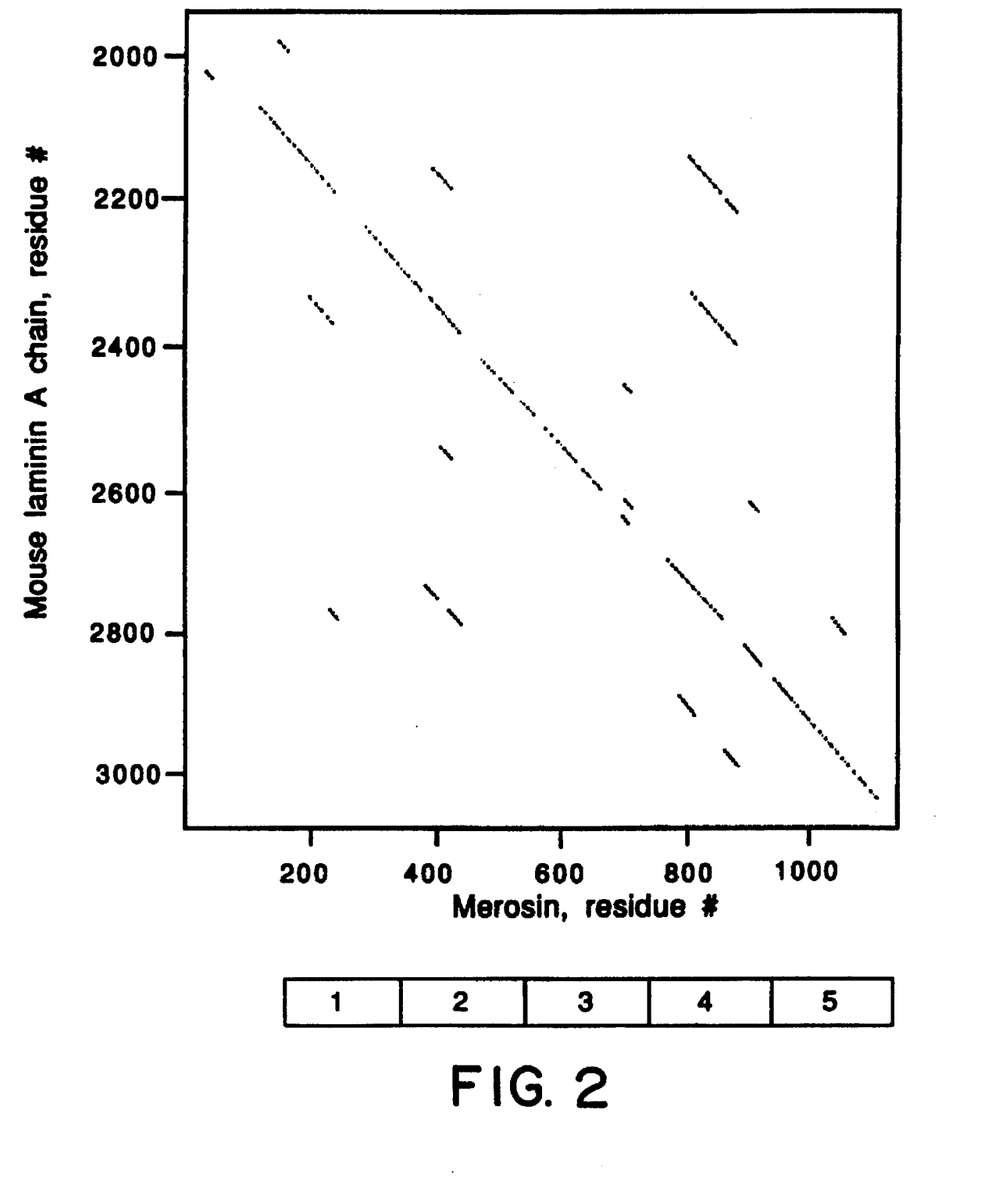
FIG. 2 shows a comparison of the amino acid sequences of merosin and the COOH-terminal portion of the mouse laminin A chain by dot matrix plotting. Sequences were compared using the Micro Genie matrix comparison program. The frame was set at eight amino acids with a minimal match of 40%.

With regard to the present invention, the cDNA shown in FIG. 1 or any portion of it can be reproduced for cloning and expression purposes by amplifying the desired sequence with PCR and cloning it into a suitable vector as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art.

Monoclonal and polyclonal antibodies against merosin were prepared according to procedures well known in the art. The specificity of the antibodies is examined by carrying out enzyme immunoassays and immunoblotting of placental extracts.

Monoclonal antibodies are prepared by immunizing an animal with material containing the protein, such as an extract of human placenta tissue, followed by isolating antibody-producing hybridoma cells, as is well known in the art. (See, for example, Harlow and Lane, ANTIBODIES: A LABORATORY MANUAL, Cold Spring Harbor, 1988, and the references cited therein, all which are incorporated herein by reference.) Antimerosin antibodies are selected by performing immunofluorescence analysis of tissue sections where merosin is localized in the basement membranes of trophoblasts, striated muscle and Schwann cells, but not the membranes of most other tissues. The identification of antibodies is confirmed by immunoblotting and immunoprecipitation which reveals one or more of the polypeptides described above. The appropriate hybridoma is reactive with purified merosin or merosin fragments. Merosin fragments can be prepared by expressing the merosin cDNA shown in FIG. 1 in a prokaryotic or eukaryotic expression vector as described above.

Alternatively, antimerosin antibodies can be prepared by immunizing an animal with synthetic peptides or recombinant protein fragments prepared from the sequence shown in FIG. 1 as is well known in the art. One sequence demonstrated to be suitable for antibody production comprises amino acid residues shown in FIG. 1. Selection of antimerosin antibodies is performed as described above.

The COOH-terminal portion of merosin is structurally related to the COOH-terminus of the laminin A-chain. However, the amino acid sequence of merosin is 61% and 62% different from the homologous portions of mouse and human laminin A chains, respectively. Affinity purified antibodies stain two bands, suggesting that the merosin polypeptide is processed into two fragments of 300 kD and 80 kD respectively.

cDNA clones for merosin A chain were isolated from a human placental lambda gt11 cDNA expression library using affinity purified antibodies specific for merosin. Two cDNA clones, designated 271 and 225, with inserts of 3.6 and 1.7 kb respectively were selected for sequencing. The nucleic acid sequence of the cDNA revealed a 3.4 kb open reading frame followed by a 155 bp untranslated 3' region. The cDNA and deduced amino acid sequences are shown in FIG. 1. $NH_2$-terminal amino acid sequences of the fragments isolated from peptic or chymotryptic digests of placenta, and the $NH_2$-terminal amino acid sequences of a 16 kD fragment generated with thrombin (Table I) were contained within the deduced sequence, thus defining the clones as merosin cDNA. RNA blot analysis revealed a single transcript of about 10 kb in human placental RNA.

The deduced partial sequence of merosin comprises 1130 amino acids and contains 13 potential sites of N-glycosylation. The sequence includes five repeats of about 190 amino acids. These repeats contain a conserved seven amino acid long sequence, LFVGGLP or variations thereof. This is followed 17–21 and 40–43 residues later by cysteines most of which are preceded by glycines. The average identity among the five repeats is about 25%.

Comparative analysis of the amino acid sequence of merosin with known proteins revealed a striking similarity to the mouse and human laminin A chains. No other significant similarities were found upon search of the data banks. The five repeats of merosin are also present in the COOH-terminal portion of the laminin A chain. The overall identity between the merosin sequence and the corresponding portion of the mouse laminin A chain is 39%.

The invention also provides a means to determine the degree of differentiation of a cell. It has been discovered that cells which are highly differentiated contain little or no merosin. Thus, a cell having a greater amount of merosin than another cell will be more highly differentiated. The term "substantial presence of merosin" means having an amount of merosin which is greater than a trace amount and thus, indicates a highly differentiated cell.

It has further been discovered that malignant tumors have an insubstantial amount of merosin compared to non-malignant tumors. The precise amount of merosin depends on the specific tumor and can be determined by one skilled in the art given the teaching of this invention.

It has still further been discovered that merosin production can be induced by contacting a cell capable of merosin production, i.e., mesenchymal, with a cell of matrices which induce merosin production.

The following examples are intended to illustrate but not to limit the invention.

EXAMPLE I

Purification of Merosin

Screening of cDNA Library

A human placental cDNA library in lambda gt11 was screened using affinity purified antibodies to denatured 65 kD chymotrypsin fragment of merosin (Table I) as described in Leivo and Engvall, supra. The identity of the isolated cDNA clones was confirmed immunologically following the procedure described by Argraves et al., J. Cell Biol. 105, 1183–1190 (1987) which is incorporated herein by reference.

Determination and Analysis of cDNA Sequences cDNA inserts were cleaved with various restriction enzymes, and fragments subcloned into either M13mp19(+) (Bethesda Research Laboratories, Gaithersburg, Md.) or Bluescript SK M13(+) (Stratagene Cloning Systems, La Jolla, Calif.). Nucleic acid sequencing was done by the dideoxy chain termination method of Sanger et al. using deoxyadenosine 5'-α-[$^{35}$S]thiophosphate (New England Nuclear, Boston, Mass.) and a kit from USB (Cleveland, Ohio). Some areas were sequenced using 15-base oligonucleotide primers synthesized using a DNA synthesizer (Applied Biosystems, Foster City, Calif.). Sequence analysis was done using the MicroGenie program (Beckman). Homology searches were carried out using Bionet with EMBL, Genbank, NBRF/PIR and Swiss-Prot databases.

Protein Sequencing

A 55 kD merosin fragment was isolated from a pepsin digest of human placenta using monoclonal antibody affinity chromatography as described in Leivo and Engvall, supra. The pepsin fragment of merosin was digested further with thrombin and a 16 kD fragment was selected for sequence analysis. The merosin fragments were electrophoretically separated on a 10 to 20% gradient polyacrylamide gel in the presence of $NaDodSO_4$, blotted onto polyvinylidene difluoride membranes (Millipore, Boston, Mass.) and sequenced on an Applied Biosystems sequenator as described by Matsudaira, J. Biol. Chem. 262 10035–10038 (1987) incorporated by reference herein.

RNA-blot Analysis

The 800 bp EcoR1 fragment from clone 225 was propagated in the Bluescript vector and labeled with [$^{32}$P]dCTP using the oligo labeling kit from Pharmacia LKB (Piscataway, N.J.). The radiolabeled probe was hybridized to a blot containing RNA from human placenta (Clontech, Palo Alto, Calif.).

Synthetic Peptides, Antibody, Production, and Immunoblotting

Two 13 amino acid long peptides CNNFGLDLKADDKI and CSIVDIDTNQEENI were synthesized based on amino acid sequences deduced from the cDNA sequence. The cysteine at the $NH_2$-terminus of these peptides was added to facilitate coupling to carrier protein. The peptides were coupled to keyhole limpet hemocyanin using m-maleimidobenzoyl-N-hydroxysuccinimide ester (Pierce Chemical Co., Rockford, Ill.) according to O'Sullivan et al. (Anal. Biochem 100, 100–108 (1979) incorporated by reference herein. The resulting conjugates were emulsified in Freund's complete adjuvant and injected into rabbits. Boosting immunizations of the conjugate in Freund's incomplete adjuvant were provided one and two months later. The dose of each injection was equivalent to 0.6 mg of peptide. Blood was collected 10 days after the third injection. The antisera obtained were tested against the glutaraldehyde-cross linked peptides in ELISA and against $NaDodSO_4$ extracts of tissue and isolated proteins in immunoblotting as described in Leivo and Engvall, supra.

Figure 3A:
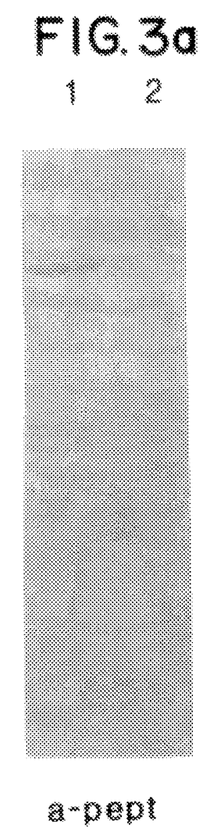
FIGS. 3a–c shows immunoblotting of placental extract with peptide antiserum. $NaDodSO_4$ extract of placenta (lanes 1) and the purified fragment of merosin from a pepsin digest of placenta (lanes 2) were electrophoresed on a 2–16% gradient acrylamide gel in the presence of $NaDodSO_4$ and transferred to nitrocellulose. The blot in (a) was stained with a peptide antiserum raised to a 13-amino acid peptide corresponding to residues 475–488 in FIG. 2. The blot in (b) was stained with monoclonal antibody that recognizes COOH-terminal fragments of merosin. For comparison, a blot of mouse laminin was stained with anti-laminin (c). Arrowhead shows the position of the top of the separating gel and numbers (kDa) indicated the positions of molecular weight markers.
Figure 3B:
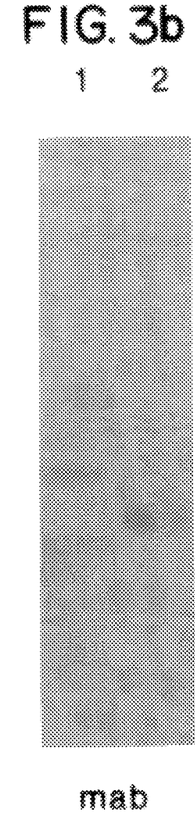
Figure 3C:
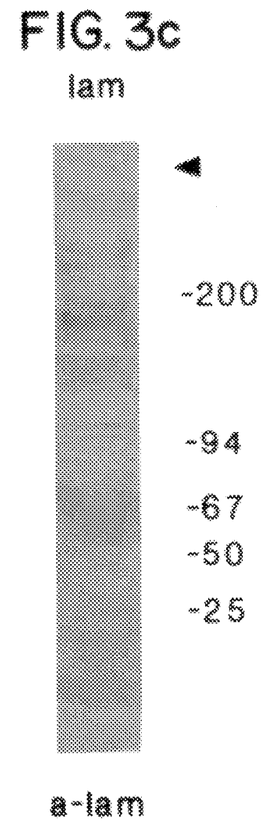

The length of the open reading frame of the merosin cDNA indicated that the mature merosin polypeptide was much larger than the 80 kD fragment identified originally in placental extracts. The deduced amino acid sequence suggested that the 65 kD fragment and the 80 kD tissue polypeptide are COOH-terminal fragments of merosin. The missing portion of the intact merosin polypeptide was identified after synthesizing two 13-amino acid long peptides from the part of the deduced amino acid presumed to be $NH_2$-terminal of the 80 kD fragment (residues 475–488 and 457–469 in FIG. 1). Immunization of rabbits with these peptides resulted in antisera which, in immunoblotting, stained a polypeptide of about 300 kD in $NaDodSO_4$-extracts of placenta. This anti-peptide antisera did not react with the 80 kD or the 65 kD COOH-terminal fragments of merosin. The presence of the 80 kD fragment in the same extract was revealed by a monoclonal antibody (FIG. 3b, lane 1). Antibodies affinity purified from the anti-peptide antiserum on immobilized peptide also stained the 300 kD band. The other peptide antiserum and preimmune sera did not give any staining in immunoblotting. These results suggest that the merosin polypeptide is processed into two fragments of 300 kD and 80 kD, respectively.

Isolation of Intact Merosin from Placenta

Merosin was then isolated using methods previously employed in the isolation of laminin from mouse tissues, Paulsson et al., Eur. J. Biochem, 166: 11–19 (1987) incorporated by reference herein. These methods are based on the selective solubilization of laminin from basement membranes with EDTA-containing buffers. When human placenta was sequentially extracted with a neutral buffer and with the same buffer containing EDTA, merosin antigenic activity was found mainly in the EDTA extract. Merosin could be precipitated from the extract with either 4M NaCl or 40% saturated ammonium sulphate. Upon gel filtration on Sepharose 6B, merosin antigenic activity eluted in the void volume peak. It bound to DEAE cellulose and was eluted at about 0.2M NaCl.

FIG. 4 shows $NaDodSO_4$-polyacrylamide gel electrophoresis, electron microscopy after rotary shadowing, and ELISA analysis of the peak merosin-containing fraction from DEAE-cellulose chromatography. The predominant component in this fraction had a molecular weight of about 700 kDa, slightly smaller than the 800 kDa rat laminin, as determined by gel electrophoresis (FIG. 4a). After reduction with mercaptoethanol, the merosin fraction contained polypeptides of about 500 kDa, 300 kDa, and 180–200 kDa in addition to some minor components of 60–90 kDa (FIG. 4a). The synthetic peptide antiserum bound to the 600 kDa and 300 kDa bands in immunoblotting. Antibodies against the COOH-terminal fragment of merosin bound to an 80 kDa band.

Figure 4A:
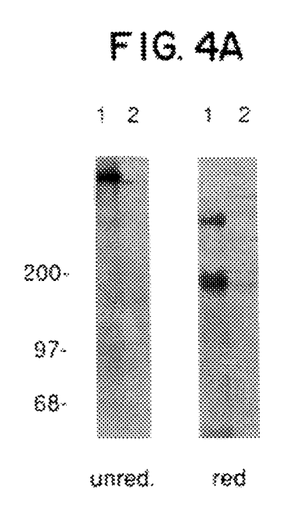
FIGS. 4a–c shows an analysis of intact merosin from placenta. A: $NaDodSO_4$-polyacrylamide gel electrophoresis of rat laminin (lane 1) and the merosin-containing fraction from human placenta (lane 2). Positions of molecular weight markers are shown on the left. B: Electron microscopy after rotary shadowing of the merosin-containing preparation. C: ELISA in microtiter wells coated with the merosin-containing preparation (FIG. 4C-1) and in wells coated with the large pepsin fragment of laminin (FIG. 4C-2). The antibodies were 3E5 (■; anti-B1), 2E8 (●; anti-B2), 11D5 (Δ; anti-A), and 2G9 (▲; ani-merosin).
Figure 4B:
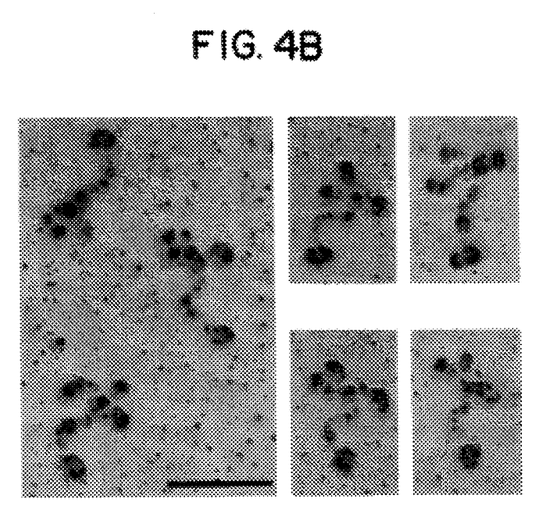

Electron microscopy after rotary shadowing was used to further characterize the merosin fraction. Cross-shaped images strongly resembling mouse and rat laminin were the predominant structures seen (FIG. 4b).

Figure 4C:
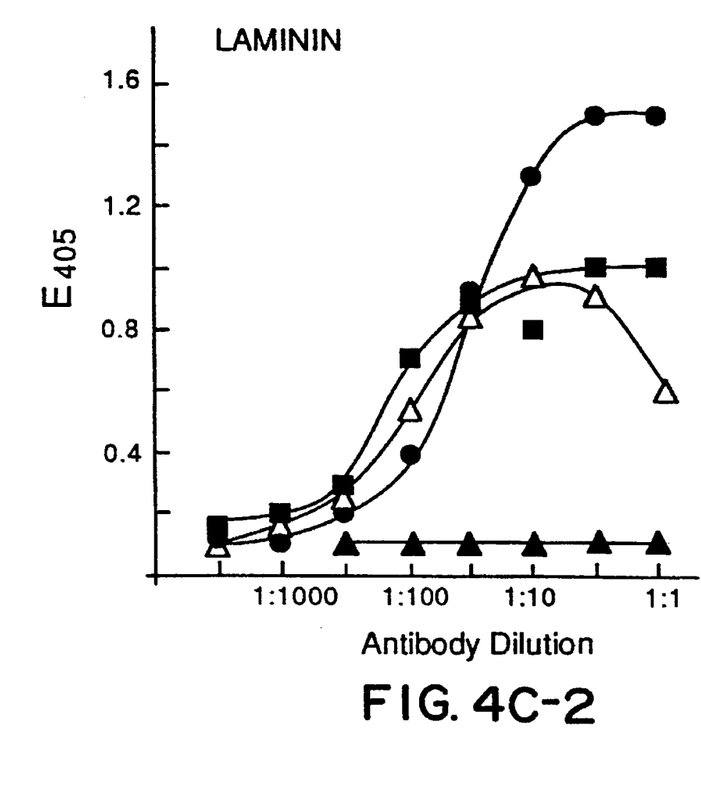
Figure 4C:
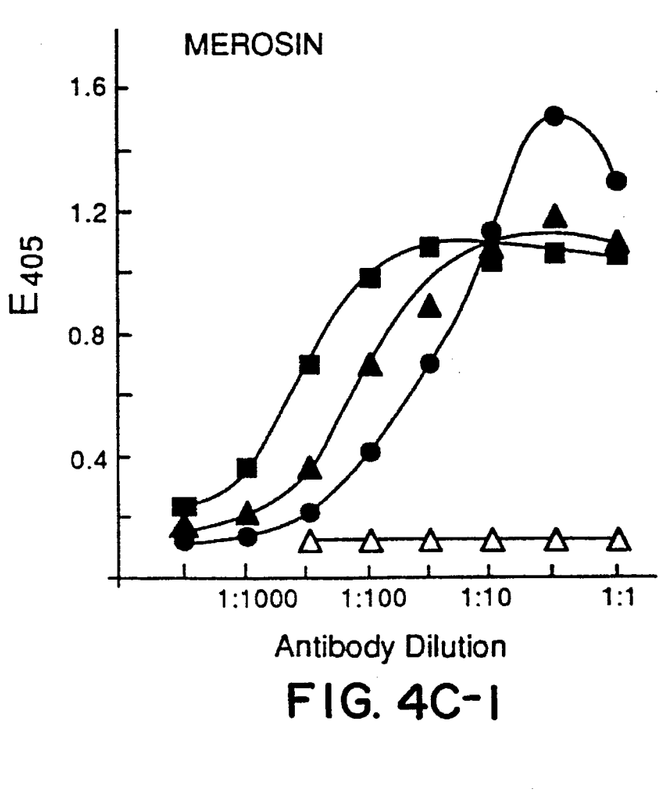

Analysis of the fraction by ELISA with merosin-specific and laminin subunit-specific monoclonal antibodies showed that the preparation contained the merosin polypeptide and the laminin B1 and B2 light chains. No reactivity was obtained with laminin heavy chain-specific antibodies (FIG. 4C-1). The truncated pepsin fragment of laminin, isolated with laminin heavy chain-specific monoclonal antibody, reacted with antibodies specific for the heavy chain as well as with antibodies specific for the B1 and B2 chains. This laminin preparation did not react with merosin antibodies (FIG. 4C-2). These results show that the high molecular weight, laminin-like molecule isolated from EDTA-extracts of placenta contained no detectable laminin heavy chain but contained laminin light chains associated with the merosin heavy chain.

EXAMPLE II

Merosin Activity

Merosin Promotes Cell Attachment

Cell attachment promotion by merosin was determined by methods well known in the art and set forth in Engvall and Ruoslahti, Collagen Rel. Res., 3: 359–369 (1983) hereby incorporated by reference. Briefly, polystyrene microtiter plates (Flow Laboratories, Irvine, Calif.) were coated with various proteins by incubating the wells with 100 µl of different concentrations of the protein in PBS for 3–16 h at room temperature. Nonbound protein was removed by three washes in PBS. In some experiments, the wells with protein solution were air dried at 37° C. and then washed. Cells were trypsinized and washed twice with 0.5 mg/ml soy bean trypsin inhibitor in EMEM. A suspension of approximately 250,000 cells per ml EMEM with 10 mM HEPES was prepared and 0.1 ml was added to each well already containing 0.1 ml EMEM. The plate was then incubated at 37° C. for 30–90 min in an atmosphere of 10% $CO_2$ in air. Cell attachment was evaluated by one or more of the following methods: 1) Nonattached cells were removed and counted; 2) attached cells were fixed, stained with toluidine blue, and counted using an Artek cell counter (Dynatech Corporation, Alexandria, Va.); or 3) the light absorbed by the fixed and stained cells was measured using an automatic ELISA reader (Multiscan, Flow Laboratories). When laminin was tested in solution, it was serially diluted in the plate with a solution of 1 mg/ml BSA in EMEM containing 10 mM HEPES before adding the cells. All assays were done with samples in triplicates.

The cell lines in table 1 have been tested for cell attachment to merosin. Successful attachment is indicated as a "+." The better the attachment the more "+'s."

TABLE 1

| Cell Line | Degree of Attachment | |
|---|---|---|
| | Merosin | Laminin |
| JAR, Chonocarcinoma | − | ++ |
| Endothelial Cells | − | +++ |
| SKLMS, Muscle | ++ | +++ |
| MG63, Osteosarcoma | +++ | +++ |
| U251, Glioma | +++ | +++ |
| JMR 32, Neuroblastoma | +++ | +++ |

The results show that merosin promotes attachment by many but not all types of cells.

Merosin Promotes Neurite Outgrowth

Neurite promoting activity by merosin was determined by known methods as set forth in Engvall et al., J. Cell Biol., 103: 2457–2465 (1986) and Manthorpe et al., A Dissection and Tissue Culture, Manual of the Nervous System, 322–326 (1989), Alan R. Liss, Inc., both of which are hereby incorporated by reference. Briefly, embryonic day 8 chick ciliary ganglion neuronal cultures were used. Polyornithine-coated tissue culture plastic wells (6-mm diameter, 96-well microplates) were treated with 5 µg/ml of human laminin or merosin in PBS for 2–3 h at 37° C. The wells were washed once with 100 µl PBS containing 1% BSA. 100 µl culture medium (Dulbecco's modified Eagle's basal medium supplemented with 0.5% BSA, $8\times10^{-7}$M insulin, $3.3\times10^{-2}$M glucose, $2.6\times10^{-2}$M $NaHCO_3$, $2\times10^{-3}$M L-glutamine, 100 µm/ml penicillin, and 100 trophic units/ml ciliary neuronotrophic factor) containing 1,000 neurons was added. glutaraldehyde for 20 min., washed with water, and stained with 0.1% toluidine blue in water. About 150 neurons were observed microscopically for each culture condition. Neurons were recorded as neurite-bearing if they possessed at least 50 µm of total neurite length.

In addition, surfaces were coated with 100 µg/ml polyoruithine (PORN) for attachment. 25 µg/ml laminin or merosin were then added for neurite outgrowth. Cells were allowed to extend neurites for 72 hours. The degree of promotion is set forth in table 2. Promotion of neurite growth is indicated as a "+." The greater the promotion, the more "+'s."

TABLE 2

|        | No Protein | Laminin | Merosin |
|--------|------------|---------|---------|
| No Porn | –         | –       | –       |
| Porn   | +          | +++     | +++     |

The results show merosin is a promotor of neurite outgrowth and, as such, is as efficient as laminin. This suggests that for certain applications (clinical) merosin would be better than laminin for nerve regeneration because it may not have e.g. angiogenic activity.

EXAMPLE III

Merosin Distribution in Human Schwann Cell Neoplasms

Experimental Design

The expression of the basement membrane proteins merosin and laminin was studied immunohistochemically in a series of benign and malignant schwannomas and plexiform neurofibromas. Fresh tissue samples were frozen in liquid nitrogen. Monoclonal antibodies to merosin and laminin were applies to frozen sections, and indirect immunoperoxidase or indirect immunofluorescence techniques were used to detect the two proteins in tissues. The results are described in Leivo et al., Laboratory Investigation, 61: 426–432 (1989). This reference and the references cited therein are hereby incorporated by reference.

Methods

Tissue Material

Human neurogenic tumors were obtained fresh without fixation at the Department of Pathology, University of Helsinki. In one instance tissue was derived from the autopsy of a patient with yon Recklinghausen's disease who died of a buccal malignant schwannoma. The tissue samples were frozen in liquid nitrogen and embedded in Tissue-Tek OCT (Miles, Naperville, Ill.). The frozen sections were air-dried for 1–2 hours and fixed in acetone. Part of each tissue sample was fixed in formalin and embedded in paraffin for conventional histologic evaluation using hematoxylin-eosin.

Antibodies

Monoclonal antibodies raised to the reduced and alkylated 65-kDa polypeptide fragment of merosin were used. These antibodies detect denatured human merosin, and they blotted an 80-kDa polypeptide band in sodium dodecyl sulfate extracts of human placenta. The following clones of these antibodies given identical staining results were used: 5H2, 4E10, 2G9, 4H2, 1F6, 2E10, and 2D10. Staining results identical to those obtained with monoclonal antibodies have also been obtained in normal tissues with a polyclonal antiserum to merosin. Monoclonal antibodies to nearly intact human laminin have been described, Engvall et al. supra. The monoclonal antibody 2E8 that blots the 200-kDa B1 chain of laminin transferred from sodium dodecyl sulfate-polyacrylamide gels was used.

In immunohistochemical characterization of the Schwann cell tumors, we used a polyclonal rabbit antibody to bovine S-100 protein (Dakopatts, Glostrup, Denmark) at 1:300 dilution and a monoclonal antibody to glial fibrillary acidic protein (Labsystems, Helsinki, Finland) at 1:30 dilution.

Immunohistochemistry

Frozen sections were treated with hybridoma culture medial at 1:2–1:5 dilution. The primary mouse antibodies were applied on sections for 30 minutes or overnight, followed by a 30-minute incubation with biotinylated rabbit antimouse IgG anti-serum (Dako, Copenhagen, Denmark) at 1:500 dilution. Finally, the bound biotin was detected with avidin combined in vitro with biotinylated peroxidase (AB Complex, Dakopatts), both diluted at 1:160. The color was developed with 3-amino-9-ethylcarbazole (Sigma, St. Louis, Mo.) supplemented with 0.02% hydrogen peroxide. In some cases, fluorescein isothiocyanate-coupled goat antimouse IgG (Bio-Rad, Richmond, Calif.) was used to detect bound primary antibodies in indirect immunofluorescence.

For controls of specificity for the staining of merosin, normal mouse serum (1:10) or phosphate-buffered saline were used instead of the hybridoma medium. Controls of specificity for the staining of laminin by monoclonal antibodies have been documented. No significant staining was observed in control experiments. The preparations stained with the immunoperoxidase technique were lightly counterstained with Mayer's hemalum (Merck, Darmstadt, West Germany) to show nuclei. Immunoperoxidase stainings and immunofluorescence preparations were observed and photographed in a Zeiss Axiophot microscope equipped for epi-illumination.

Results

Four human schwannomas, two plexiform neurofibromas, and four malignant schwannomas were examined.

Schwannomas

Two schwannomas were retroperitoneal; one was mediastinal, and one was from the gastric wall exhibiting the histological features of gastric schwannomas. Histologically, all schwannomas showed a relatively uniform spindle cell morphology with focally palisading arrangement of nuclei. Two cases showed an alternating pattern of cellular and loose areas, representing the so-called Antoni A and Antoni B areas, respectively. Electron microscopic examination performed in three cases disclosed spindle cells rich in rough endoplasmic reticulum exhibiting multiple slender cell processes covered by prominent deposition of basement membrane material. These findings were compatible with the ultrastructural features of schwannomas. In immunohistological studies, all schwannomas were strongly positive for S-100 protein. Glial fibrillary acidic protein (GFAP) was focally seen in three cases.

Prominent staining for laminin was seen in parallel layers of basement membranes in the cellular areas and in the entire thickness of the walls of all blood vessels. The loose, less cellular areas of the tumors and the connective tissue sheaths around vessel walls contained no immunoreactive laminin. The cellular areas including the Verocay bodies contained no or only negligible amounts of merosin. However, distinct staining for merosin was regularly seen at the interface where the cellular areas bordered the loose stromal areas or where the cellular areas bordered vascular septa.

Plexiform Neurofibromas

Two plexiform neurofibromas were from nerve trunks of the subcutis of the back and the mediastinum of patients with von Recklinghausen's disease. These tumors represented enlarged tortuous nerve trunks containing wavy collagen and spindle cells compatible with Schwann cells and fibroblasts. In both tumors, merosin and laminin were colocalized in the form of linear immunoreactivity along basement membranes outlining the tortuous nerve fascicles. Laminin was also found in vessel walls. However, no merosin was seen in this location.

Malignant Schwannomas

These tumors originated from deep nerve trunks of femoral, retroperitoneal, and buccal tissues in patients with von Recklinghausen's disease. Histologically they represented malignant high grade spindle cell sarcomas with pronounced mitotic activity and focal areas of necrosis. The malignant schwannomas showed only minimal focal immunostaining for S-100 protein. No staining with antibody to GFAP was detected.

There was only minor focal staining for laminin in some perivascular tumor cells. All vessel walls were, however, strongly positive for laminin. Three of the four malignant schwannomas showed no immunostaining for merosin in the tumor cells. In contrast to laminin, only the external edges of vessel walls showed some staining. In sections where remnants of the original nerve trunks were microscopically identified, staining for merosin outlined the Schwann cell basement membranes of residual normal axons blending into merosin-negative tumor cell areas. A fibrous capsule surrounding malignant schwannomas was negative for merosin. However, in the adjacent striated muscle tissue, the basement membranes were positive for merosin. In one case, small but definite amounts of merosin were seen as punctate deposits between the tumor cells. In this case, a similar pattern of immunostaining for laminin was seen.

Discussion

In brief, the distribution of merosin in schwannomas was more restricted than that of laminin, whereas in plexiform neurofibromas both proteins were present in the same location. No significant amounts of either protein were seen in malignant schwannomas.

In schwannomas, a strong staining for laminin was observed in basement membranes of the cellular Antoni A areas. In contrast, these areas were devoid of merosin. Immunoreactive merosin was seen at the border zone between tumor cells and vessel walls. The discordant distribution of the two basement membrane proteins in schwannomas differs from the situation in normal peripheral nerves where both the merosin and laminin are seen in the Schwann cell basement membranes. The reasons for this difference are unknown, but the result may reflect different biological roles for the two basement membrane proteins. Ultrastructurally, no apparent difference seems to exist between the neoplastic basement membranes of schwannomas and the normal basement membranes surrounding Schwann cells.

The presence of merosin only at the boundaries of the schwannoma cells and nonSchwann cell mesenchymal components demonstrates that the expression of merosin may be induced by a contact or an interaction of schwannoma cells with mesenchymal tissues or extracellular matrices and that no expression occurs by isolated schwannoma cells even in relatively well-differentiated tumors. Analogously, Schwann cells in peripheral nerves may require interactions with other cell types of the nerve fascicles such as the neurons, endoneurial fibroblasts, or perineurial cells for synthesis and/or deposition of merosin. It has been shown that the myelination and assembly of Schwann cell basal lamina in the developing nerve in vitro depend on interactions between the Schwann cell and neuron. Likewise, secretion of type IV collagen by cultured Schwann cells is modulated by a contact with neurons.

In plexiform neurofibromas, large amounts of both merosin and laminin were seen in an identical location. These neoplasms contain increased numbers of Schwann cells and perineurial cells as well as some residual axons contained within an intact perineurial sheath and enlarge the nerve fascicles. Thus, a relatively well-organized tissue architecture presumably essential for the expression of merosin is maintained. The presence of various cell elements within these nerve fascicles allows for many cellular contacts and interactions, and apparently some of these are essential for the secretion of merosin.

In the malignant schwannomas of this study, both merosin and laminin were absent or only minimally expressed. The concomitant lack of immunohistological markers for Schwann cell differentiation such as S-100 protein and GFAP suggests that these tumors are neurogenous sarcomas at a low level of Schwann cell differentiation.

Many cultured human cell lines including schwannomas have been examined for the biosynthesis and secretion of merosin, but the protein has not been found in cell cultures. Conversely, biosynthesis if laminin, type IV collagen, heparan sulfate proteoglycan, and entactin has been repeatedly shown in Schwann cell and schwannoma cell cultures. Moreover, in solid choriocarcinomas merosin was expressed by cells of the intermediate trophoblast type. No merosin could be detected in cultured choriocarcinoma cell lines, although these cell lines synthesized laminin. Apparently, cultured and neoplastic Schwann cells and other cells lose the capacity to secrete merosin but retain some other matrix proteins characteristic of the corresponding mature cells.

During mouse development, significant quantities of merosin were found in muscles and peripheral nerves only after birth. Together with the present results this indicates that the expression of merosin is a feature of mature cells that could be expected only in well-differentiated normal or neoplastic Schwann cells.

Although the invention has been described with reference to the presently-preferred embodiment, it should be understood that various modifications can be made without departing from the spirit of the invention. Accordingly, the invention is limited only by the following claims.

What is claimed is:

1. A method of promoting neurite growth comprising,
   a) contacting a neuron with a purified protein, designated merosin, composed of four polypeptides having apparent molecular weights of 300 kDa, 200 kDa, 200 kDa and 80 as determined by SDS-PAGE under reducing conditions, the 300 kDa polypeptide being joined to the 200 kDa polypeptides by disulfide bonds, and wherein the 80 and 300 kDa polypeptides comprising at least portions of the amino acid sequence shown in FIG. 1, and
   b) allowing the neuron to remain in contact with merosin for sufficient time to promote neurite growth.

* * * * *

UNITED STATES PATENT AND TRADEMARK OFFICE
CERTIFICATE OF CORRECTION

PATENT NO.   : 5,624,905
DATED        : April 29, 1997
INVENTOR(S)  : Engvall et al.

It is certified that error appears in the above-identified patent and that said Letters Patent is hereby corrected as shown below:

Column 2,
Line 48, please delete "ani-merosin)." and replace with -- anti-merosin). --

Column 8,
Line 55, please delete "$_2$M" and replace with -- $^2$M --.
Line 57, after "added." please insert -- Cultures were fixed after 3 h by the addition of 20 µl 2% --.

Column 9,
Line 37, please delete "yon" and replace with -- von --.

Column 12,
Lines 48 and 51, please insert -- kDa -- after "80".

Signed and Sealed this

Sixteenth Day of April, 2002

JAMES E. ROGAN
Director of the United States Patent and Trademark Office